United States Patent [19]

Van Pool

[11] Patent Number: 4,479,018
[45] Date of Patent: Oct. 23, 1984

[54] COMBINED ETHER AND ALKYLATE PRODUCTION

[75] Inventor: Joe Van Pool, Bartlesville, Okla.

[73] Assignee: Phillips Petroleum Company, Bartlesville, Okla.

[21] Appl. No.: 297,461

[22] Filed: Aug. 28, 1981

[51] Int. Cl.$^3$ ............................................. C07C 41/06
[52] U.S. Cl. .................................... 568/697; 585/723; 585/331
[58] Field of Search ................. 568/697; 585/723, 331

[56] References Cited

U.S. PATENT DOCUMENTS

| | | |
|---|---|---|
| 2,720,547 | 10/1955 | Wolff et al. |
| 3,206,390 | 9/1965 | Van Pool |
| 3,213,154 | 10/1965 | Bauer |
| 3,309,882 | 3/1967 | Cabanaw ............................. 203/2 |
| 3,726,942 | 4/1973 | Louder |
| 3,846,088 | 11/1974 | Brown et al. |
| 3,912,463 | 10/1975 | Kozlowski et al. |
| 3,966,586 | 6/1976 | Owen ................................. 568/697 |

Primary Examiner—Howard T. Mars
Attorney, Agent, or Firm—Bernhard H. Geissler

[57] ABSTRACT

Introduction of undesirable materials through liquid containing vessels of an ether forming unit into an alkylation unit is prevented by pressurizing one or more of these liquid containing vessels of the ether forming unit with a gas which is compatible with both the ether forming reaction and the alkylation reaction and which has a boiling point to keep it in essentially the gas phase in the pressurized vessel and to keep it in the liquid or dissolved form in the overhead accumulator associated with the fractionator of the alkylation unit (if said gas is present in the accumulator at all).

6 Claims, 1 Drawing Figure

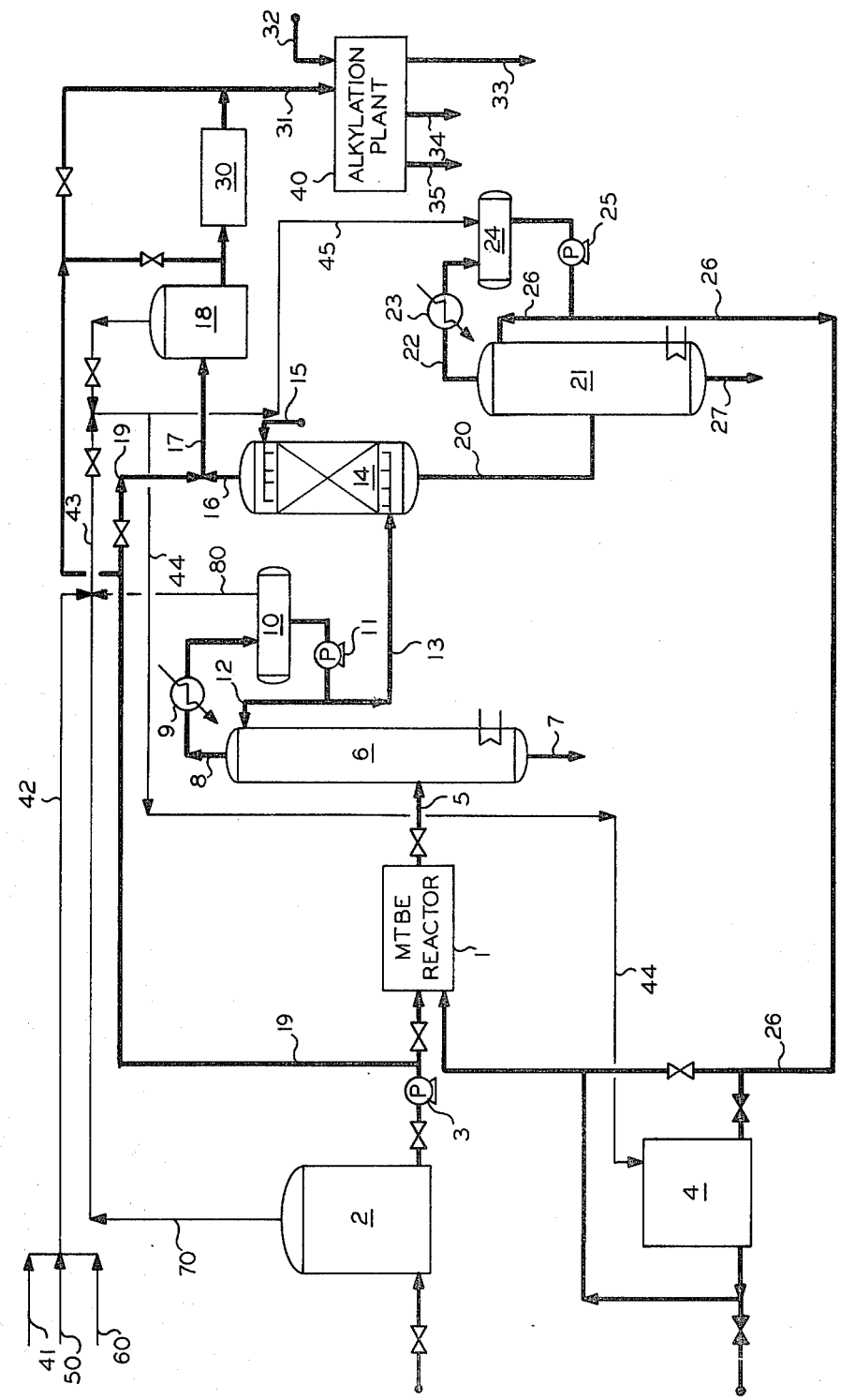

COMBINED ETHER AND ALKYLATE PRODUCTION

BACKGROUND OF THE INVENTION

It is known in the art to produce ether by the reaction of an alcohol and an olefin. It is also known in the art to produce high octane hydrocarbons by an HF alkylation reaction of an olefin and an isoparaffin. Both the ether and the alkylate are valuable fuel feedstocks.

It is also known in the art to produce MTBE (methyl tertiary butyl ether) by reacting butylenes and methanol and to charge the unreacted butylenes to an alkylation plant in which the butylenes and an isoparaffin such as isobutane are reacted to form high octane gasoline components.

Whereas the above discussed technologies have been developed to a rather mature stage, several problems have remained. Thus, the combination process of ether formation and alkylation outlined above has the disadvantage that the olefin stream coming from the ether production may entrain dissolved materials which are either harmful to the alkylation reaction as such or which tend to be released in the fractionation of the alkylation product in gaseous form thus entraining, for instance, HF and/or propane.

THE INVENTION

It is thus one object of this invention to provide a combined process for the production of ether and alkylate with reduced risk of losses of materials from the alkylation zone caused by undesirable materials entering the alkylation unit from the ether unit.

A further object of this invention is to provide a combined ether and alkylate forming process in which the introduction of impurities into both the ether unit and the alkylation unit is minimized. A yet further object of this invention is to provide a combined ether forming and alkylate forming process which makes the two units, namely the ether unit and the alkylation unit, even more compatible.

These and other objects, advantages, details, features and embodiments of this invention will become apparent to those skilled in the art from the following detailed description of the invention, the appended claims and the drawing which shows a schematic flow diagram of an embodiment of this invention.

In accordance with this invention, an ether forming and alkylate forming combination process is provided in which unreacted olefins from the ether forming unit are at least partially transferred to the alkylate forming unit. The transferring of substances detrimental to the alkylation unit from the ether unit is avoided by pressurizing one or more of the liquid collection vessels containing liquids which are introduced into the ether unit and by using a gas for this pressurization which is compatible both with the ether forming unit and the alkylation unit and which has a boiling point below the operating temperature of the vessel at its operating pressure where it is used for the pressurization and a boiling point which is above the operating temperature of an overhead collector at its operating pressure which overhead collector is associated with a fractionation zone in the alkylation unit.

By this specific way of pressurizing vessels containing liquids for the ether unit, the introduction of undesirable gases into this unit is effectively prevented and the pressurizing gas is such that it is both compatible with the two reactions, namely, the ether forming reaction and the alkylation reaction, but is also of such a nature that the gas used for the pressurization, which may be carried into the alkylation unit, will not function as a gas entraining, for instance, HF and/or propane, from a fractionator in the alkylation unit. More specifically, the present invention improves a process for the production of both an ether and an alkylate. This process comprises reacting an olefin and an alcohol to form a first reaction mixture comprising the ether, the alcohol and the olefin. From this first reaction the ether is recovered as a first product of the process. In the ether forming unit one or more liquids are accumulated in one or more vessels for later use in the ether forming reaction. An olefin-containing stream is separated from the above-mentioned first reaction mixture. This olefin-containing stream, or at least a portion thereof, is reacted with an isoparaffin in the presence of an HF alkylation catalyst under HF alkylation conditions to form a second reaction mixture comprising alkylate. This alkylate is then recovered from the second reaction mixture as a second product of the combination process. This alkylate is generally recovered as the bottoms stream from a fractionation zone in which at least a portion of the organic phase of the second reaction mixture is fractionated. The fractionation zone is provided with an overhead accumulator in which cooled and condensed overhead effluent from the fractionation zone is accumulated. In accordance with this invention, the vessel for liquid accumulation in the ether forming unit is pressurized with a gas which is compatible with both the ether forming reaction and the HF alkylation reaction. Furthermore, this gas is of such a nature that it will be essentially in gaseous form in the vessel so pressurized under the vessel conditions and that it will be essentially in liquid or dissolved form in the overhead accumulator of the fractionator of the HF alkylation unit, if such gas is present in such fractionator at all. The gas used for pressurizing the vessel may dissolve to a certain extent the liquid accumulated in the vessel but the boiling point of the pressurizing material at the operating pressure of the vessel will be below the operating temperature of this vessel. Correspondingly, if some of the gas used for the pressurization of the vessel for liquid accumulation in the ether forming unit will be carried into the fractionation zone of the HF alkylation unit, this gas will predominantly be present therein as liquid or gas dissolved in a liquid in the overhead accumulator associated with such a fractionation zone although a very small quantity of such gas may exist in the gas phase of such an accumulator. Thus, the boiling point of the pressurizing material at the operating pressure of the overhead accumulator will be above the operating temperature of the overhead accumulator associated with the fractionation zone of the alkylation unit.

In accordance with the preferred embodiment, the gas used in this invention for pressurizing the liquid collection vessel of the ether unit is a nonaromatic hydrocarbon gas having at least three carbon atoms. Particularly preferred gases are paraffins and monoolefins having three to five carbon atoms. Examples of such hydrocarbon gases which can advantageously be used to pressurize the liquid accumulation vessels are propylene, butylenes, propane and butanes.

It is most advantageous and in accordance with the invention therefore preferred to use one or more hydrocarbons as said gas for the pressurization of said vessel which are of the same kind as those hydrocarbons present in the HF alkylation unit. It is most preferred to use an olefin as said gas which is a reaction component in either the ether forming reaction, or the alkylation reaction or in both reactions.

Mixtures of gases as defined above can be used for the purposes of this invention.

The ether forming reaction of the combination process of this invention is known in the art both generally and in many of its details. Reference is made to U.S. Pat. No. 3,846,088 in which such an ether production particularly for the production of methyl tertiary butyl ether is described. The present invention is applicable to a variety of ether forming units. Usually the ether forming reaction is carried out by contacting alkyl alcohols having one to three carbon atoms, preferably methanol, with monoolefins having four to six carbon atoms under ether forming conditions in the presence of an ether forming catalyst. Preferably, olefins having four or five carbon atoms and containing a tertiary carbon atom connected via a double bond to another carbon atom such as isobutylene and methyl isobutylene are used in the ether forming reaction. Typical ether forming catalysts include commercially available "Amberlyst 15", "Dowey 50" and "Nalcite HCR". Ether forming reaction conditions and catalysts are well known in the art and disclosed, for instance, in U.S. Pat. No. 3,846,088 which is herewith incorporated by reference.

Similarly, the alkylation unit of the combination process of this invention is well known. U.S. Pat. Nos. 3,213,157, 3,211,536 and 3,309,882 describe such HF alkylation processes. These patents are incorporated herewith by reference. In the conventional HF alkylation reaction liquid isoparaffin and liquid olefin are contacted with liquid HF catalyst to form a reaction mixture. After liquid-liquid phase separation of this reaction mixture an alkylate is removed from the organic phase as one product of the process. The olefins useful in HF alkylation reactions and particularly in the combination process of this invention are olefins having three to five carbon atoms. The paraffins used for the alkylation reaction are generally isoparaffins having four to six carbon atoms, isobutane being particularly preferred.

Among the vessels for accumulating liquids which liquids are used in the ether forming reactions are alcohol storage vessels, accumulators associated with the ether fractionator from which the ether is withdrawn as a bottom stream and from which the unreacted alcohol and olefin mixture is withdrawn as an overhead stream which is then condensed and accumulated as a liquid in such accumulator vessels, as well as alcohol accumulator vessels associated with the alcohol fractionator in which the alcohol washed out with water from the ether fractionator overhead stream is separated from such water and leaves the alcohol fractionator overhead while the water is removed as a bottom stream. The pressurization of each of these vessels with the gas as defined above prevents any undesirable gas or liquid to flow into the vessel and into the fluid accumulated in the vessel and thus prevents the introduction of undesirable fluids through such vessels into the ether forming loop and subsequently into the alkylation unit. It is presently preferred to pressurize the alcohol storage vessels and/or the alcohol accumulator vessels.

The gas used for the pressurization of the liquid storage or accumulation vessels, in accordance with this invention, are essentially free of such materials as air, oxygen, nitrogen, hydrogen, methane, ethane, ethylene and fuel gas. The following description of the drawing illustrates further preferred embodiments of this invention but is not intended to unduly limit the scope thereof.

In an MTBE reactor, olefins (and particularly isobutylene) withdrawn from an olefin storage drum 2 via a pump 3 and methanol withdrawn from a methanol storage drum 4 are reacted to form a reaction mixture which is withdrawn from the MTBE reactor system 1 via line 5. This reaction mixture comprises the ether formed, unreacted olefins and unreacted alcohol. The ether reaction mixture is fractionated in a fractionator 6. From this fractionator 6 the ether is withdrawn via conduit 7 as a first product of the process. The overhead stream leaving the fractionator 6 via line 8 contains the unreacted olefin (isobutylene) and methanol. The gaseous overhead stream is cooled by indirect heat exchange means 9 and the condensed liquid is accumulated in accumulator 10. A portion of the accumulated liquid is reintroduced via pump means 11 and conduit 12 into the fractionator 6 as reflux. The remaining portion of the accumulated liquid is passed via line 13 to an alcohol washing column 14 into which water is introduced via line 15. An olefin stream being substantially free of methanol (in this specific example containing mainly butylene as the olefin) leaves the alcohol washing column 14 via line 16. This olefin containing stream is passed via line 17 to a surge tank 18 for olefins. Additional olefins can be passed to this surge tank via line 19 from the storage drum 2.

Wet methanol leaves the alcohol washing column 14 via line 20 and is introduced into the alcohol fractionator 21. Essentially water free methanol leaves the methanol fractionator 21 via line 22 and is cooled by indirect exchanger in cooler 23 and the liquid alcohol (in this example methanol) is accumulated in the alcohol accumulator 24. A portion of the so accumulated alcohol is passed via pump 25 and line 26 to the alcohol fractionator 21 as reflux. The remaining or yield portion of the alcohol accumulated in the accumulator 24 is passed via line 26 to either the alcohol storage vessel 4 or the ether reaction zone 1. Water is withdrawn the bottom of the alcohol fractionator 21 via line 27. This water in part can be recycled to line 15 as a portion of the wash water for removing the alcohol from the olefin.

Typical operating conditions of the individual units of the ether unit described above are contained in the following table.

| | Reference | Temperature °F. | Pressure psia |
|---|---|---|---|
| Storage Drum | 2 | 100 | 50 |
| Ether Fractionator, top portion | 6 | 122 | 80 |
| Ether Fractionator, bottom portion | 6 | 236 | 85 |
| Accumulator | 10 | 109 | 75 |
| Alcohol Washing Column | 14 | 100 | 120 |
| Alcohol Fractionator, top | 21 | 169 | 23 |
| Alcohol Fractionator, bottom | 21 | 240 | 25 |
| Accumulator | 24 | 164 | 20 |
| Alcohol Storage Tank | 4 | 100 | slightly above atmospheric |

-continued

| Reference | Temperature °F. | Pressure psia |
|---|---|---|
| | | pressure |

An olefin feedstream comprising olefins from the surge tank 18 and/or olefin from the storage drum 2 are introduced after an optional passage through an olefin dryer 30 into the alkylation unit 40 via conduit 31. Also introduced into this alkylation unit 40 is an isoparaffin stream via conduit 32. From the alkylation unit an alkylate stream is withdrawn via line 33, a paraffin stream (usually n-butane) is withdrawn via line 34 and a propane stream is withdrawn via line 35. The alkylation unit comprises an alkylation reaction zone in which the isobutane is alkylated with the olefin(s) in the presence of HF catalyst, a phase separator in which the liquid organic phase is separated from the liquid HF phase, and one or more fractionators in which the organic phase is fractionated into various hydrocarbon streams. The unit 40 is not shown in more detail in the drawing since these alkylation units are well known in the art.

In accordance with this invention, one or more of the liquid accumulating or storing vessels associated with the ether unit, more specifically the methanol storage unit 4 and/or the alcohol accumulator 24 are pressurized with a gas which is compatible with both the ether forming reaction and the alkylation reaction and which has a boiling point which is such that under the operating pressure of the pressurized vessel the gas will exist mainly in gaseous form whereas under the operating pressure and temperature of the overhead accumulator associated with the alkylation fractionator such gas (if present there) exists mainly in the liquid phase or in the dissolved state with none or only very little of said gas in the gaseous phase of this alkylation fractionator accumulator, thereby minimizing the quantity of gas which must be vented from the accumulator, which venting causes loss of HF and even propane from the system, which loss occurs when pressurizing gases comprising at least one of air, oxygen, nitrogen, hydrogen, methane, ethane, ethylene and fuel gas. Thus, in accordance with this invention, it is possible to use propane vapor from a propane storage means via conduits 41, 42, 43 and 44 to pressurize the methanol storage drum 4 and via conduit 41, 42, 43 and 45 to pressurize the alcohol accumulator 24. Similarly, a normal butane vapor stream from line 50 or an isobutane vapor stream via line 60 can be used in the same manner.

Another source for the pressure maintenance on the liquid vessels described can be the storage drum 2 for the olefin. Olefin vapor can be passed via line 70 to pressurize the alcohol storage vessel 4 and/or the alcohol accumulator 24.

Still another source for pressure maintenance on the liquid vessels can be vapor from accumulator 10 via conduit 80.

Reasonable variations and modifications which will be become apparent to those skilled in the art can be made in this invention without departing from spirit and scope thereof.

What is claimed:

1. In a combination process of ether production and alkylate production comprising
    (a) reacting an olefin and an alcohol to form a first reaction mixture comprising ether, alcohol and olefin,
    (b) recovering ether from said first reaction mixture as a first product of the combination process,
    (c) accumulating a liquid in a vessel and thereafter using said liquid in the reaction step (a),
    (d) separating an olefin containing stream from said first reaction mixture,
    (e) reacting at least a portion of said olefin containing stream with isoparaffin and in the presence of an HF alkylation catalyst under HF alkylation conditions to form a second reaction mixture comprising alkylate,
    (f) recoverying alkylate from said second reaction mixture as a further product of the process as the bottom stream from a fractionation zone in which at least a portion of the organic phase of said second reaction mixture is fractionated and which fractionation zone is provided with an overhead accumulator in which cooled condensed overhead effluent from said fractionation zone is accumulated,
    the improvement comprising
    pressurizing said vessel for liquid accumulation with a pressurizing material in gaseous form, which material is essentially free of air, oxygen, nitrogen, hydrogen, methane, ethane, and ethylene, which material is compatible with the HF alkylation reaction and with the ether forming reaction and which pressurizing material has a boiling point above the operating temperature of said overhead accumulator at its operating pressure and which pressurizing material has a boiling point below the operating temperature of said vessel at its operating pressure, and which material is a non-aromatic hydrocarbon having at least three carbon atoms, or with a mixture of such pressurizing materials.

2. Process in accordance with claim 1 wherein said pressurizing material is an olefin.

3. Process in accordance with claim 2 wherein said pressurizing material is an olefin which is the same kind of olefin as the olefin used in step (a).

4. Process in accordance with claim 3 wherein said pressurizing material is an olefin which is the same kind of olefin as the olefin used in the ether forming reaction step (a) and in the alkylation reaction step (e).

5. In a combination process of ether production and alkylate production comprising
    (a) reacting an olefin and an alcohol to form a first reaction mixture comprising ether, alcohol and olefin,
    (b) recovering ether from said first reaction mixture as a first product of the combination process,
    (c) accumulating a liquid in a vessel and then using said liquid in the reaction step (a),
    (d) separating an olefin containing stream from said first reaction mixture,
    (e) reacting at least a portion of said olefin containing stream with isoparaffin and in the presence of an HF alkylation catalyst under HF alkylation conditions to form a second reaction mixture comprising alkylate,
    (f) recoverying alkylate from said second reaction mixture as a further product of the process as the bottom stream from a fractionation zone in which at least a portion of the organic phase of said second reaction mixture is fractionated and which fractionation zone is provided with an overhead accumulator in which cooled condensed overhead effluent from said fractionation zone is accumulated, the improvement comprising pressurizing said vessel for liquid accumulation with a monoolefin gas having three to five carbon atoms.

6. Process in accordance with claim 5 wherein said monoolefin is an olefin of the same kind as the olefin used for the ether forming reaction step (a) and/or for the alkylation reaction step (e).

* * * * *